United States Patent [19]

Plotkin et al.

[11] Patent Number: 5,358,978
[45] Date of Patent: Oct. 25, 1994

[54] ALKENYL ETHER POLYCARBONATES

[75] Inventors: Jeffrey S. Plotkin, Monsey, N.Y.; Fulvio J. Vara, Chester, N.J.; James A. Dougherty, Pequannock, N.J.; Paul D. Taylor, West Milford, N.J.; Kolazi S. Narayanan, Palisades Park, N.J.

[73] Assignee: ISP Investments Inc., Wilmington, Del.

[21] Appl. No.: 13,269

[22] Filed: Feb. 3, 1993

Related U.S. Application Data

[62] Division of Ser. No. 490,867, Mar. 9, 1990, Pat. No. 5,254,710.

[51] Int. Cl.$^5$ .................. C08F 2/50; C08F 220/18; C08F 220/26
[52] U.S. Cl. .................. 522/163; 522/181; 522/182; 522/25; 522/31; 522/96; 522/170
[58] Field of Search .................. 522/25, 31, 163, 181, 522/182, 170, 96; 558/266

[56] References Cited

U.S. PATENT DOCUMENTS

| | | | |
|---|---|---|---|
| 2,385,933 | 10/1945 | Muskat et al. | 260/78 |
| 4,156,035 | 5/1979 | Tsao et al. | 522/25 |
| 4,230,548 | 10/1980 | Adelmann et al. | 528/196 |
| 4,273,726 | 6/1981 | Altuglu | 558/266 |
| 4,293,503 | 10/1981 | Young | 558/266 |
| 4,654,379 | 3/1987 | Lapin | 522/25 |
| 5,045,572 | 9/1991 | Plotkin et al. | 522/181 |
| 5,200,437 | 4/1993 | Dougherty et al. | 522/181 |
| 5,254,710 | 10/1993 | Plotkin et al. | 558/266 |
| 5,276,174 | 1/1994 | Plotkin et al. | 558/266 |

*Primary Examiner*—Susan W. Berman
*Attorney, Agent, or Firm*—Marilyn J. Maue; Joshua J. Ward

[57] ABSTRACT

This invention relates to alkenyl ether polycarbonates having the formula $$A-OCO[R''(OR'')_m OCO]_n ROCH=CHR'$$

wherein A is selected from the group consisting of lower alkyl and R'HC=CHOR—, R and R'' are each independently a divalent radical having from 2 to 20 carbon atoms and are selected from the group of alkylene, mono- or poly- alkoxylated alkylene, alkenylene, alkynylene, arylene, alkarylene and aralkylene radicals, which radicals are optionally substituted with halo, alkyl, cyano, nitro or alkoxy; R' is hydrogen or lower alkyl; (n) has a value of from 1 to 10 and (m) has a value of from 0 to 10; with the proviso that R'' contains at least 3 carbon atoms when m is zero. The invention also concerns the preparation and use of said alkenyl ether polycarbonates.

6 Claims, No Drawings

ALKENYL ETHER POLYCARBONATES

This is a division of application Ser. No. 490,867, filed Mar. 9, 1990, now U.S. Pat. 5,254,710.

In one aspect the invention relates to alkenyl ether polycarbonate compounds and in another aspect to their use as coatings or as reactive diluents for acrylates, vinyl ethers and epoxides in cationic or hybrid cationic radiation curing. In still another aspect, the invention relates to the preparation of the novel carbonates defined herein.

BACKGROUND OF THE INVENTION

Certain radiation curable coatings and films such as those formed from the acrylates, particularly trimethylol propane triacrylate, trimethacrylate, pentaerythritol triacrylate, and hexanediol diacylate or methacrylate, are in great demand because of their rapid curing properties. However, these compounds are normally highly viscous liquids or solids and thus are unsuitable as diluents for other polymeric components of a radiation curable formulation. Indeed, such compounds themselves require the incorporation of a diluent or solvent for uniform substrate coating, control of coating thickness and curing at low temperatures. Accordingly, low viscosity monofunctional diluents are usually included in their formulations. While these diluents are reactive, they materially reduce the cross-linked density of the finished product and consequently lower abrasion resistance and ability to withstand chemical attack.

Although solvents have been used to reduce viscosity, they are detrimental in radiation curing due to their volatility which presents problems for uniform composition control unless their evaporation prior to radiant exposure is effected. Obviously, such procedure extends processing time and may pose environmental drawbacks.

To some extent, the drawbacks of high viscosity monomers can be reduced by curing at elevated temperatures. However, this alternative significantly adds to the cost of the overall operation in the expenditure of energy, temperature control and loss of more volatile components in the composition or blistering of the coating resulting from entrained volatiles.

Since acrylate monomers are not conducive to cationically induced radiation curing, they require free radical systems which are oxygen inhibited unless effected in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus,. the cured product often contains significant amounts of unpolymerized components. Accordingly, it is an aim of research to develop a monomer having the beneficial properties of acrylates but which is amenable to radiation curing at a rapid rate by cationically induced polymerization which is not oxygen inhibited and which permits continued polymerization after removal from the source of radiation exposure.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

The inherent deficiencies of the acrylate systems can be partially overcome by the use of epoxy resins. Epoxy resins can be polymerized by normal radiation techniques using cationic photoinitiators such as iodonium, sulfonium and ferrocene salts of hexafluorophosphate, hexafluoroantemonate and hexafluoroarsonate to produce a tack free film. Although in such formulations tack free products are almost immediately obtained, polymerization of the mixture is incomplete. It is well known that the polymerization of epoxy resins is extremely slow and requires as much as several days to achieve their ultimate physical properties. Thus, thermal curing is often employed to increase the rate of polymerization.

Certain allyl compounds also have been used as coatings; however these monomers and their oligomers are not readily curable by cationic radiation. Thermal curing is generally required to increase the rate of polymerization. While allyl ethers of polyethylene glycols are curable by UV light, they require a free radical initiated reaction which proceeds at a slow rate, generally over a period of from 2 to 10 hours in order to reach completion.

Accordingly, it is an object of this invention to overcome the above deficiencies and to provide a commercially feasible and economical process for producing radiation curable compounds which are homopolymerizable and which may be combined with other polymers or monomers not normally curable by radiation at high speed in the presence of oxygen.

Another object is to provide film forming compounds which have excellent resistance to abrasion and chemicals such as solvents, acids and basis.

Another object is to provide a simple and economical process for the copolymerization of the present compounds disposed as protective coatings on a substrate.

Still another object is to provide compounds capable of forming hydrogels by hydrolysis.

Still another object is to provide photoresist compounds capable of high image resolution upon exposure to a source of radiation.

Yet another object is to provide a substrate with an improved coating which has good adhesion and elongation properties.

These and other objects will become apparent from the following description and disclosure.

THE INVENTION

In accordance with this invention there is provided alkenyl ether polycarbonates having the formula

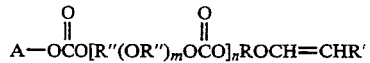

$$A-OCO[R''(OR'')_mOCO]_nROCH=CHR'$$

wherein A is selected from the group consisting of lower alkyl and R'HC=CHOR—, R and R" are each independently a divalent radical having from 2 to 20 carbon atoms and are selected from the group of alkylene, mono- or poly- alkoxylated alkylene, alkenylene, alkynylene, arylene, alkarylene and alalkylene radicals, which radicals are optionally substituted with halo, alkyl, cyano, nitro or alkoxy; R' is hydrogen or lower alkyl; (n) has a value of from 1 to 10 and (m) has a value of from 0 to 10; with the proviso that R" contains at least 3 carbon atoms when m is zero.

Preferred species of the present alkenyl ether polycarbonates are those wherein R' is hydrogen and A is R'HC=CHOR— or —CH$_3$; R is C$_2$ to C$_8$ alkylene; R" is C$_2$ to C$_6$ alkylene; m has a value of from 0 to 6 when R" contains at least 3 carbon atoms and m has a value of from 1 to 6 when R" contains 2 carbon atoms.

The products of this invention or their oligomers can be homopolymerized or copolymerized with other functional monomers or oligomers to provide useful coatings when applied on a substrate and cured. The products, being substantially linear and mono- or difunctional do not polymerize to the same high density structure as is obtained in the homopolymers of copending patent application Ser. No. 07/491,362, now U.S. Pat. No. 5,276,174 entitled ALK-1-ENYLOXY CARBONATES, filed concurrently herewith. Hence the present homopolymers are more flexible and have good elongation properties while still retaining high chemical resistance and toughness.

The present polycarbonates are synthesized by reacting a hydroxyalkyl alk-1-enyl ether, a diol and a dialkyl carbonate according to the following equation.

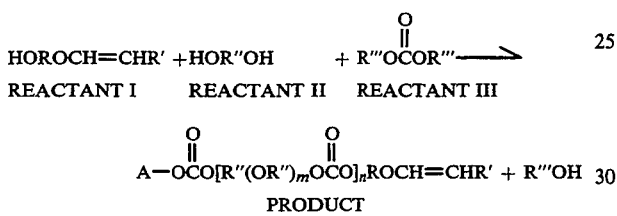

PRODUCT wherein each R''' is represented by lower alkyl and R, R', R", A, m and n are as defined above. The reaction is carried out under mild conditions such as a temperature of between about 65° C. and about 130° C. under a pressure ranging from about atmospheric to about 50 psig. for a period of from about 1 to about 30 hours, preferably at a temperature of between about 75° and about 125° C. under ambient pressure for a period of from about 1.5 to about 10 hours. This reaction is effected in an oxygen-free atmosphere under a blanket of inert gas, e.g. nitrogen. The reaction is promoted with between about 0.01 and about 5 wt. %, preferably between about 0.3 and about 2 wt. % of a base catalyst including such catalysts as sodium or potassium alkoxides, particularly methoxides; sodium or potassium metal; sodium or potassium methoxylate, hydroxide, hydride or phenoxide, alkaline earth metal hydroxides or alkoxides and alkaline or alkali earth salts of reactant I. In carrying out the reaction, it is recommended that reactants II and III be mixed prior to contact with reactant I.

Generally, the mole ratio of reactant I to II to reactant III can vary within the range of between about 1:10:20 and about 1:0.5:2, preferably between about 4:1:4 and about 2:1:2. Although the reaction does not require the use of a diluent, an inert liquid at a concentration of up to 50 wt. % of the reaction mixture can be employed. Suitable diluents include toluene, xylene, benzene, alkyl ethers, N-methylpyrrolidone, butyrolactone, ethyl acetate and the like which are normally liquid and have a boiling point below that of the reaction product.

It is found that the product composition can be varied depending upon the initial ratio of reactants I, II and III. Specifically an excess of reactant III produces polycarbonates wherein A is lower alkyl; whereas an excess of reactant I produces a disubstituted product wherein A is R'CH=CHOR—. Also, n in the alkenyloxy polycarbonate product largely depends on the mole ratio of reactant III with respect to reactant II. Thus, where a high proportion of III is employed, the value of n is increased. Conversely, where a low proportion of III is employed, the value of n is low.

Alternatively, the dialkenyloxy dicarbonate products of this invention can be prepared by reacting the diol (HOR"OH) with a dialkenyloxy monocarbonate e.g. a product of our copending patent application Ser. No. 07/491,395, now abandoned entitled ALKENYL ETHER CARBONATES, filed concurrently herewith. The reaction conditions for this alternative reaction are substantially the same as those described above except that the mole ratio of diol to carbonate reactant is about 1:2. This reaction can be defined by the equation

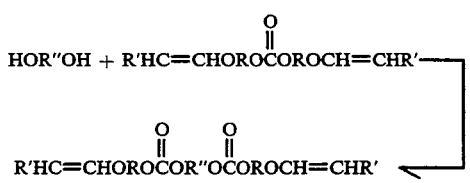

The substantially linear products, particularly the dialkenyloxy substituted products, of this invention provide cross-linked films and protective coatings when subjected to a source of radiation such as UV light, electron beam, laser emission and the like. The products can be cured with a cationic photoinitiator under ambient conditions at a rapid rate. Suitable cationic photoinitiators include an onium salt, for example the triphenyl sulfonium salt of phosphorous hexafluoride, diphenyl iodium salt, phenyl onium salts or aryl alkyl onium salts and the like.

The initiators suitable to effect polymerization reactions of the present invention can also comprise a mixture including the above named cationic initiators and a free radical initiator to provide a hybrid initiated system. Suitable free radical initiators include 1-hydrocyclohexyl phenyl ketone (e.g. IRGACURE 184), 2-hydroxy-2-methyl-1-phenyl-1-propan-1-one (DAROCUR 1173), 2,2-dichloro-1-(4-phenoxyphenyl) ethanone (SANDORAY 1000) and the like. Other free radical and cationic initiators which are suitably employed in this invention are those described by M. J. M. Abadie, Advantages and Development of Photochemical Initiators, in the European Coatings Journal 5/1988 pages 350–358. When such initiator mixtures are employed, the free radical component can comprise up to 75%, preferably between about 30 and about 70%, of the initiator component. A particularly preferred initiator mixture includes between about 30 wt. % and about 40 wt. % of FX-512 and between about 60 and about 70% of IRGACURE 184. The present cationic initiator or cationic/free radical initiator mixtures are recommended for cross linking blends of the present vinyl ether carbonate and a polymerizable vinyl ether or epoxide comonomer. When the blend includes an acrylate, initiator mixtures are recommended. The total amount of initiator employed is generally between about 0.1 and about 5 wt. % with respect to reactant or reactants.

Usually, exposure for less than one second is sufficient to provide a completely cross-linked homopolymer or copolymer. UV light radiation dosages at room temperature of from about 100 to about 1,500 milli J/cm² are effective and dosages of from about 200 to about 600 milli J/cm² are preferred. Equivalent dosages for curing are employed when using alternative sources of radiation. For example, curing with electron beam radiation can be carried out at between about 0.5 and about 20 Mrads, preferably between about 1 and about 10 Mrads. Specific techniques for radiation curing are well known, thus further amplification is not required.

As inferred above, the present products can be mixed with a vinyl ether, epoxide, acrylate or vinyloxy alkyl urethane monomer or polymer to incorporate and combine the advantages of instant compounds with the beneficial properties of those or other coating materials which otherwise would not be amenable to cationic radiation curing. Examples of monomers or polymers with which the present products can be combined to form coatings include dibutyl ethylene oxide, tetramethyl ethylene oxide, diethyl ethylene oxide, the diglycidyl ether of bisphenol A, epihalohydrin, butadiene monoxide, vinyl cyclohexane epoxide, alkyl methacrylates and acrylates, vinyloxy butyl urethane, cyclo aliphatic epoxides and other functional monomers and polymers which possess properties beneficial in durable protective coatings. When such comonomeric coatings are employed, the mixture contains at least 25% of the present alkenyl ether polycarbonate.

The homopolymerized and copolymerized products of this invention have high resistance to solvents, acids and bases and form hard abrasion resistant films and coatings, possessing good substrate substantivity. The individual products of this invention, as monomers or oligomers or as mixtures thereof are also useful as chemical intermediates and as materials which, upon hydrolysis, are capable of forming hydrogels. Also, because of their high radiation sensitivity, the present compounds are suitable as photoresist materials.

Having generally described the invention, reference is now had to the accompanying examples which illustrate preferred embodiments thereof but which are not to be construed as limiting to the scope of the invention as more broadly set forth above and in the appended claims.

EXAMPLE 1

A 500 ml, round bottom flask was charged with 30 g of triethylene glycol (0.2 mole), 105 g bis(ethenyloxybutyl) carbonate (0.41 mole) and 0.1 g sodium methoxide. The flask was heated under vacuum of 3 mm Hg at 100°–105° C. in a Kugelrohr apparatus for a period of 4.5 hours, after which a total of 44.3 g of distillate was collected. The distillate was analyzed by gas chromatography (GC), and identified as a mixture of 95% hydroxybutyl vinyl ether, 3.8% bis(ethenyloxybutyl) carbonate and 0.8% triethylene glycol.

The residue containing carbonate product weighed 90 g. To the residue was added 2 g Nuchar charcoal and the mixture was heated to 60° C. under vacuum for 30 minutes and filtered.

The filtrate was a colorless liquid, weighing 83.0 g (yield of about 90%). ¹H NMR and IR data identified the product as having the structure

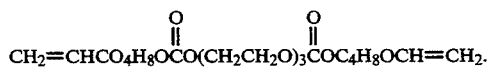

The IR spectrum showed absence of OH frequency. About 98% conversion was achieved.

EXAMPLE 2

Example 1 was repeated except that 21 g of diethylene glycol (0.2 mole) was used in the place of 30 g triethylene glycol.

The flask contents were heated under vacuum, 3–5 mm Hg at 100° C. for a period of 4.5 hours and 43.1 g distillate containing a mixture of hydroxybutyl vinyl ether and the carbonate reactant was removed.

The contents of the flask was worked up as described in Example 1. The filtrate was a clear colorless liquid weighing 83.3 g indicating about 90% yield.

IR spectrum analysis of the product showed total absence of OH signals. ¹H NMR and IR data identifed the product as having the structure

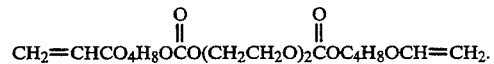

More than 99% conversion was obtained.

EXAMPLE 3

A 500 ml round bottom flask was charged with 36 g butenediol (0.41 mole), 220 g bis(ethenyloxybutyl) carbonate (0.85 mole) and 0.4 g sodium methoxide. The procedure described in Example 1 was repeated except that the flask was heated at 100° C. under vacuum of 6 mm Hg for hours.

During this period, 166.5 g of distillate was collected. The reaction mixture was heated at 130° C. under 0.5 mm Hg vacuum, until distillation ceased and an additional 12.5 g of distillate was collected.

The pot content was worked up as described in Example 1 except that only 1 g of charcoal was used. A colorless viscous liquid (67 g) which solidified on standing was obtained. The product was identified by ¹H NMR and IR spectral data as having the structure

EXAMPLE 4

A 500 ml round bottom flask was charged with 28.8 g cyclohexane dimethanol (0.2 mole), 110 g bis(ethenyloxybutyl) carbonate (0.43 mole) and NaOCH₃ 0.2 g. The procedure described in Example 1 was repeated except that the reaction mixture was heated at 100° C. for only 2.5 hours. Recovery of distillate (65.9 g) was found to contain a mixture of reactants, (about 20.0 g of bis(ethenyloxybutyl) carbonate) and 43.5 g of bis(hydroxybutyl vinyl ether).

The residue was worked up as in Example 1 with 1 g charcoal (Nuchar) heated to 90° C. for 30 minutes and filtered. The filtrate was a clear colorless viscous liquid weighing 62 g. IR and ¹H NMR spectral data identified the product as having the structure

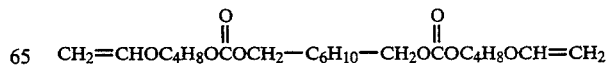

IR spectrum showed total absence of OH frequency. Greater than 98% conversion was achieved.

EXAMPLE 5

The product from Example 4 (46.7 g) was charged into a 100 ml round bottom flask and heated to 130° C. under a vacuum of 3 mm Hg for 1 hour. Distillate weighing 5 g, primarily bis(ethenyloxybutyl carbonate) was removed. Spectral analysis of the pot content showed oligomerization of Example 5 product, i.e.

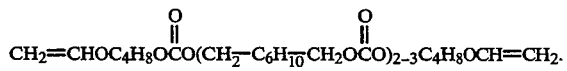

EXAMPLE 6

The procedure described in Example 1 was repeated except that the reaction mixture charged to the flask was 11 g of bisphenol A, 32.5 g bis(ethenyloxybutyl carbonate) and 1 g of KOH. The mixture was heated at 130° C. under 5 mm Hg for a period of 7 hours. The distillate was removed and $^1$H NMR identified the pot content as a mixture of the following products

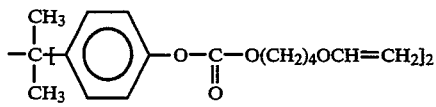

and

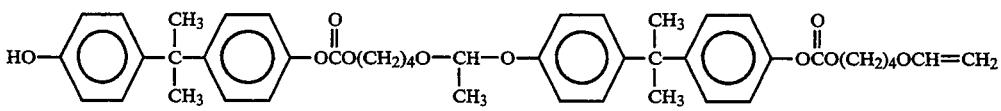

EXAMPLE 7

The procedure described in Example 1 was repeated except that the reaction mixture charged to the flask was 18.6 g. 1-dodecanol and 25.8 g bisethenyloxybutyl carbonate and 0.1 g sodium methoxide. The flask was heated at 90° C. under vacuum of 5 mm Hg for 5 hours.

During this period 13 g distillate containing a mixture of hydroxybutylvinyl ether and the carbonate reactant was removed.

The contents of the flask was worked up as in Example 1 using 1 g charcoal (Nuchar), heated to 60° C. for 30 minutes and filtered. The filtrate was a clear colorless liquid which solidified on cooling weighing 26 g. IR and $^1$H NMR spectral data identified the product as having the structure

EXAMPLE 8

Example 1 was repeated except that 62.6 g of the bis-ethoxylate of bisphenol A (dianol 22 from AKZO) was used in place of triethylene glycol. The reaction mixture was heated under vacuum at 3–5 mm Hg at 100° C. After 2 hours 52 grams of distillate was removed. The resulting yellowish liquid was treated with charcoal at 50° C., and filtered. The final product was a clear viscous liquid. The $^1$H NMR spectrum is consistent with the following structure.

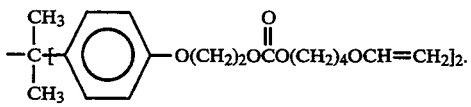

EXAMPLE 9

A four-necked 500 ml round bottom flask equipped with a mechanical stirrer, thermometer, distillation head and water condenser, additional funnel and nitrogen inlet was charged with 76 g of butanediol (0.86 mole), 150 g of dimethyl carbonate (1.7 mole), 11.6 g of hydroxybutyl vinyl ether (0.1 mole), and 1 g of sodium methoxide. The pot temperature was maintained at about 100° C. under a blanket of nitrogen for a period of 12 hours, during which an azeotrope containing methanol and dimethyl carbonate was distilled off at a head temperature of 31°–35° C.

The reaction mixture was filtered and flash distilled at 120°–150° C. under 3 mm Hg. A solid residue (A) weighing 85 g was recovered.

The residue (A) comprised 66% of n

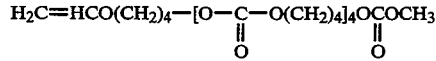

and 33% of

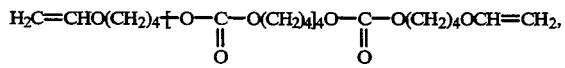

which mixture was confirmed by HNMR analysis.

EXAMPLE 10

A 28 g portion of the residue (A) described in Example 10 was charged into a 250 ml, 3 necked round bottom flask equipped with mechanical stirrer, thermometer and a vertical condenser attached to a vacuum line.

Hydroxybutyl vinyl ether (100 g) and sodium methoxide (0.2 g) were added to the residue. The flask was then heated and maintained at a temperature of 100° C., under a vacuum of 100 mm Hg, for a period of about 6.5 hours.

The content of the flask was flash distilled at 150° C. under 3 mm Hg leaving 30 g of final product (B) which was a liquid at 30°–40° C. and slowly solidified at room temperature. During the flash distillation about 90 g hydroxybutyl vinyl ether was recovered. Product B, i.e.

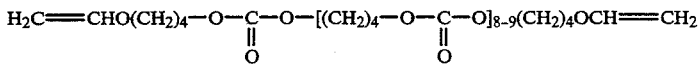

was identified by ¹HNMR analysis.

EXAMPLE 11

A four necked, 500 ml round bottom flask equipped with a mechanical stirrer, thermometer, distillation head with a water condenser and a $N_2$ inlet was charged with 70 g of butanediol (0.78 mole), 150 g of dimethyl carbonate (1.67 mole), 11.6 g of hydroxy butyl vinyl ether (0.1 mole) and 0.5 g of sodium methoxide. The flask was heated under $N_2$ by gradually raising the temperature to 105° C.; and maintained at 90° C. for 1 hour followed by continued heating up to 105° C. for a total period of 12.5 hours. During this period 90.4 g of distillate was removed at a head temperature of about 63° C. No distillate, (an azeotrope of methanol and dimethylcarbonate) came off during the distillation.

The reaction mixture was filtered and 141.6 q of the filtrate was flash distilled at 120° C. under a reduced pressure of 3 mm Hg over a period of 2 hours, after which 98 g of a solid mixture was obtained the solid product (C)

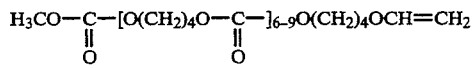

and

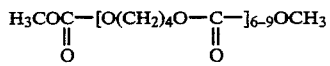

was identified by 'HNMR analysis.

The solid product C (75.4 g) was charged into a 500 ml 3-necked round-bottom flask equipped with a mechanical stirrer, thermometer-vertical water condenser and $N_2$ inlet. The condenser was connected to a source of vacuum via a trap and 100 g of hydroxybutyl vinyl ether and 0.3 g of sodium methoxide were added to the flask. The flask was heated and maintained at 100° C. at a reduced pressure of 150 mm Hg for a period of 9.5 hours. The contents of the flask was then filtered and 162.4g of filtrate was flash distilled at 110° C. under reduced pressure of 3 mm Hg during which unreacted hydroxy vinyl ether was removed, leaving 89.4 g residue which solidified on cooling. This solid product was found to be

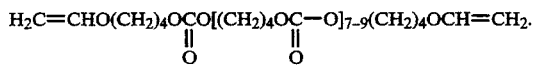

EXAMPLE 12

Example 11 was repeated except that the charge to the reactor was 50 g of residue A obtained from Example 9, 100 g of hydroxy butylvinyl ether and 0.2 g sodium methoxide. The mixture was heated to 105° C. under a vacuum of 160 mm Hg for a period of 12 hours and the crude product was then filtered. The filtrate, weighing 141 g, was flash-distilled at 100° C. under a reduced pressure of 3 mm Hg for a period of 2.5 hours. The resulting product,

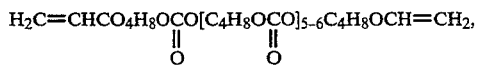

(59.7 g) was recovered and solidified on cooling to room temperature.

EXAMPLE 13

Example 9 was repeated except that the charge to the reactor contained excess dimethyl carbonate. 90 g butanediol (1 mole), 360 g dimethyl carbonate (4 moles) and 1 g sodium methoxide. The flask was heated gradually heated and maintained at 85°–95° C. for 20.5 hours during which 165.6 g distillate, an azeotrope of methanol and unreacted dimethyl carbonate, was collected at a head temperature of 42°–45° C. Analysis of a 5 g aliquot of the remaining liquid in the flask showed it to be a methyl end-capped carbonate oligomer intermediate having the structure

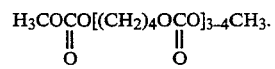

Hydroxy butylvinyl ether (250 g, 2.15 mole) was added to the flask and the temperature was raised to 135°–140° C. under a blanket of nitrogen for a period of 4 hours, during which 33 g of distillate was removed. The reaction product was filtered under suction and 350 g of the filtrate was flash-distilled at 100° C. under 3 mm Hg to remove 201 g of distillate. The oligomeric product (139 g) having the formula

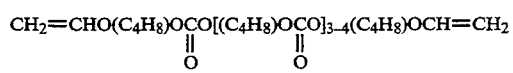

was recovered from the flask

EXAMPLE 14

A four-necked 1 liter flask equipped with a mechanical stirrer, thermometer, distillation head with a horizontal condenser, nitrogen inlet and a receiver was charged with 250 g of commercially available poly THF* (polyoxybutylene diol—250 having an average molecular weight about 250), 360 g (4 moles) of dimethyl carbonate (DMC) and 1 g titanium isopropoxide. The flask was heated and maintained at 90° C. for a period of 9 hours during which 169.5 g of distillate (an azeotrope of methanol and dimethyl carbonate) was collected at a head-temperature of 36° C.
* $HO(C_4H_8O)_{3-4}H$ Progress of the reaction was monitored periodically by ¹HNMR data and OH number. The reaction product was found to be a mixture of methyl terminated and OH terminated carbonate oligomers.

A second addition of DMC (100 g) was made to the flask and heating continued at a pot temperature 95°–97° C. under a blanket of nitrogen for 6 hours, during which 55.4 g distillate was removed. Analysis of the reaction mixture indicated residual OH group.

A third addition of DMC (100 g) was then made and heating continued at a pot temperature of 95°–101° C. for 3 hours under N₂ during which an additional 118.4 g of distillate was removed. Analysis showed the OH number of tries reaction mixture to be 85.5 mg KOH/g, indicating almost 80% conversion.

A final addition of DMC (100 g) made and, heating continued under N₂ at pot temperature 105°–115° C., during which 101.5 g distillate was collected at a head temperature of 67°–75° C. over a period of 6 hours. Thus, a total of 445 g distillate was collected. The reaction mixture, analyzed by ¹HNMR data, showed practically complete methyl terminated polycarbonate of the poly THF diol as an intermediate product, (i.e. polyoxybutylene diol). The OH number was found to be 20.8 mg KOH/g.

Hydroxybutyl vinyl ether (240 g, 2.07 moles) was then added to the flask and heating was continued at a pot temperature from 130° to 156° C. for 6.5 hours under N₂. During this period 59 g distillate, mostly methanol was removed at a head temperature about 67° C. The remaining liquid was then flash distilled at 150° C. under a reduced pressure of 3 mm Hg, leaving 311 g of a yellow oil in the flask as the final product (D).

Product D was found to have the formula

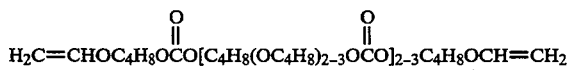

The OH number of product D 2.8 was 8.0 mg KOH/g.

EXAMPLE 15

Example 9 was repeated except that 75 g commercially available triethylene glycol (0.5 mole), 360 g dimethyl carbonate (4 moles), and 0.4 g sodium methoxide were charged to the flask. The flask was heated under N₂ at 85° C. and 96 g of distillate was collected over a period of 5 hours at a head temperature of 51° C. The remaining volatile components were removed by heating under vacuum (140–180 mm Hg) at a temperature 50°–55° C. whereupon 42.5 g additional distillate was removed at a head temperature of 42° C. ¹HNMR analysis of the intermediate product showed the composition to be methyl terminated carbonate oligomer having the formula

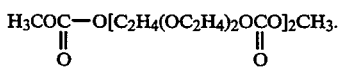

Hydroxybutyl vinyl ether (120 g, 1.04 moles) was then addecd to the flask and heating under N₂ was continued at 110° C.–160° C. over a period of 11 hours during which period 188 g of distillate was collected at a head temperature varying from 43° to 94° C. until no more distillate came off at atmospheric pressure.

The reaction mixture was then filtered and 208 g of filtrate was flash-distilled at 170° C. under 3 mm Hg over a period of 4 hours to provide 130 g of final product in the flask as pale yellow oil having the formula

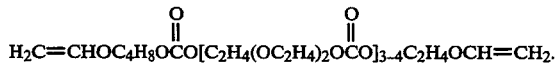

This product had an OH number=19.5 mg KOH/g, indicating greater than 97% conversion.

EXAMPLE 16

The product of Example 2 was mixed with an equal amount of a diglycidyl ether of bisphenol A (EPON-828, supplied by Shell Oil), 1 phr* of a fluorochemical surfactant (FC-430, supplied by Minnesota Mining and Manufacturing Co.) and 4 phr of cationic photoinitiator (FX-512) until a homogeneous low viscosity liquid was obtained. This mixture was then coated on an aluminum substrate in a thickness of 1.6 mil. The coated surface was exposed for less than 1 second to 400 millijoules/cm² radiation from a mercury vapor lamp. A tack-free film was produced. Coating properties reported in the following table were determined immediately after UV exposure and after a post cure of 177° C. for 15 minutes.

* parts/hundred parts of resin

| Property | After UV | Post Cured |
|---|---|---|
| Pencil Hardness (ASTM D3363) | 4B | H |
| Double MEK Rubs | >100 | >100 |
| % Adhesion (ASTM D 3359) | 0 | 100 |
| Reverse Impact (in-lbs) | — | 55 |
| Mandrel Bend (in.) (ASTM D3111) | 3/16 | ⅛ |

*parts/hundred parts of resin

EXAMPLE 17

The product of Example 3 was mixed with an equal weight of triethylene glycol divinyl ether, 1 phr fluorochemical surfactant (FC-430) and 4 phr cationic photoinitiator (FX-512) until a homogeneous low viscosity liquid was obtained. This mixture was then coated on an aluminum substrate in a thickness of 1.4 mil. The coated surface was exposed for less than 1 second to 400 millijoules/cm² radiation from a mercury vapor lamp. A tack-free film was produced. Coating properties reported in the following table were determiend immediately after UV exposure and after a post cure of 177° C. for 15 minutes.

| Property | After UV | Post Cured |
|---|---|---|
| Pencil Hardness (ASTM D3363) | <4B | F |
| Double MEK Rubs | 150 | >100 |
| % Adhesion (ASTM D 3359) | 0 | 100 |
| Reverse Impact (in-lbs) | — | 15 |
| Mandrel Bend (in.) (ASTM D3111) | ⅛ | 3/16 |

EXAMPLE 18

Example 10 was repeated except that the reaction product of Example 1 is substituted for the reaction product of Example 3. The following properties were determined for the product.

| Property | After UV | Post Cured |
|---|---|---|
| Pencil Hardness | <4B | <4B |
| Double MEK Rubs | 4 | 10 |
| % Adhesion | 0 | 70 |
| Reverse Impact (in-lbs) | — | 15 |
| Mandrel Bend (in.) | 7/16 | 5/16 |

EXAMPLE 19

Example 10 is repeated except that the reaction product of Example 4 is substituted for the reaction product of Example 3. The following properties for the product were determined.

| Property | After UV | Post Cured |
|---|---|---|
| Pencil Hardness | <4B | F |
| Double MEK Rubs | 12 | 80 |
| % Adhesion | 0 | 0 |
| Reverse Impact (in-lbs) | — | 15 |
| Mandrel Bend (in.) | ⅛ | ⅛ |

EXAMPLE 20

The product of Example 2 (50.0 gm) is mixed with 50 g of a bisphenol a epoxy acrylate oligomer (EBECRYL-3700, Radcure Specialties), 2 phr cationic photoinitiator (FX 512), 2 phr free radical photoinitiator (IRGACURE-184)* and 1 phr fluorochemical surfactant FC-430 at 50° C. until a homogeneous, low viscosity liquid is obtained. This mixture is then coated on a polyester substrate at a thickness of 0.5 mil. The coated surface is exposed to 400 millijoules/cm² radiation free coating having a good pencil hardness of about 3H, 100% adhesion and high chemical resistance is obtained.

* hydroxycyclohexyl phenyl ketone

EXAMPLE 21

The product from Example 3 (50.0 gm) is mixed with 25 g of a divinyl ether urethane oligomer (prepared as described in the Thesis of Lennart Carlsson, Department of Polymer Technology at the Royal Institute of Technology, Stockholm, Sweden, 1987); 4 phr cationic photoinitiator (FX-512), and 1 phr fluorochemical surfactant FC-430 at 50° C. until a homogeneous low viscosity liquid is obtained. This mixture is then coated on a aluminum panel in a thickness of 0.50 mil and exposed to 400 millijoules/cm² radiation from a mercury vapor lamp for less than 1 second. A tack free coating having a good pencil hardness of about 3B, a Mandrel bend of at least ⅛ inch is obtained.

It is to be understood that any of the other species of the present polycarbonates within the scope of this invention can be homopolymerized or copolymerized with the above mentioned comonomers by radiation curing in the manner described in Example 16 to provide strong, chemically resistant coatings on various substrates, e.g. glass, ceramic, metal, wood, leather and paper surfaces.

What is claimed is:

1. A polymerizable composition comprising a photoinitiator and a compound having the formula

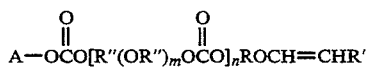

wherein A is selected from the group consisting of lower alkyl and R'HC=CHOR—; R and R" are each independently a divalent radical having from 2 to 20 carbon atoms and are selected from the group of alkylene, mono- or poly-alkoxylated alkylene, alkenylene, alkynylene, arylene, alkarylene and aralkylene radicals, which radicals are optionally substituted with halo, alkyl, cyano, nitro or alkoxy; R' is hydrogen or lower alkyl; (n) has a value of from 1 to 10 and (m) has a value of from 0 to 10; with the proviso that R" contains at least 3 carbon atoms when m is zero.

2. The composition of claim 1 wherein the composition contains a cationic photoinitiator.

3. The composition of claim 2 wherein the composition contains up to 75% of a acrylate or methacrylate compound.

4. The composition of claim 3 wherein the photoinitiator is a mixture of a cationic and a free radical photoinitiator.

5. The cured product obtained by the process which comprises applying to a substrate an effective protective coating of the composition of claim 1 and curing said coating on said substrate by exposure to an effective curing amount of radiation.

6. The cured product obtained by the process which comprises applying to a substrate an effective protective coating of the composition of claim 4 and curing said coating on said substrate by exposure to an effective curing amount of radiation.

* * * * *